United States Patent
Farrugia

(10) Patent No.: US 9,827,389 B2
(45) Date of Patent: Nov. 28, 2017

(54) BLOOD GLUCOSE REGULATION THROUGH CONTROL OF BREATHING

(75) Inventor: Steven Paul Farrugia, Lugarno (AU)

(73) Assignee: ResMed Limited (AU)

( * ) Notice: Subject to any disclaimer, the term of this patent is extended or adjusted under 35 U.S.C. 154(b) by 493 days.

(21) Appl. No.: 12/920,535

(22) PCT Filed: Mar. 5, 2009

(86) PCT No.: PCT/AU2009/000271
§ 371 (c)(1),
(2), (4) Date: Sep. 1, 2010

(87) PCT Pub. No.: WO2009/109013
PCT Pub. Date: Sep. 11, 2009

(65) Prior Publication Data
US 2011/0132370 A1   Jun. 9, 2011

Related U.S. Application Data

(60) Provisional application No. 61/068,189, filed on Mar. 5, 2008.

(51) Int. Cl.
*A61M 16/00*  (2006.01)
*A61B 5/145*  (2006.01)
(Continued)

(52) U.S. Cl.
CPC ..... *A61M 16/0051* (2013.01); *A61B 5/14532* (2013.01); *A61B 5/4818* (2013.01);
(Continued)

(58) Field of Classification Search
CPC ........ A61M 16/0051; A61M 2230/205; A61M 2205/583; A61M 2230/06;
(Continued)

(56) References Cited

U.S. PATENT DOCUMENTS

| | | |
|---|---|---|
| 4,944,310 A | 7/1990 | Sullivan |
| 4,979,509 A | 12/1990 | Hakky |

(Continued)

FOREIGN PATENT DOCUMENTS

| | | |
|---|---|---|
| WO | 2006-037184 A1 | 4/2006 |
| WO | 2007093010 A1 | 8/2007 |
| WO | WO 2007093010 A1 * | 8/2007 |

OTHER PUBLICATIONS

Cryer, P. F., 'Hypoglycemia, functional brain failure, and brain death', The Journal of Clinical Investigation, Apr. 2007, vol. 117(4), pp. 868-870.

(Continued)

*Primary Examiner* — Lynne Anderson
(74) *Attorney, Agent, or Firm* — Lerner, David, Littenberg, Krumholz & Mentlik, LLP

(57) ABSTRACT

A respiratory treatment apparatus (1) provides blood glucose monitoring and breathing control based on detected blood glucose information. In an example embodiment, a flow generator provides a flow of breathable gas at a pressure above atmospheric to a patient interface according to a pressure treatment control protocol such as a CPAP, APAP, bi-level CPAP, etc. A detector determines a blood glucose condition indicator with one or more sensors that are used to sense physiological information. In response to signals from the sensors, a controller, such as a digital signal processor, controls adjustments to the flow of breathable gas provided by the flow generator. The adjustments are determined by the controller based on the detected blood glucose indicator and/or changes thereto.

25 Claims, 3 Drawing Sheets

(51) Int. Cl.
*A61B 5/00* (2006.01)
*G06F 19/00* (2011.01)

(52) U.S. Cl.
CPC ........ *G06F 19/3481* (2013.01); *A61B 5/4035* (2013.01); *A61M 2016/0027* (2013.01); *A61M 2016/0033* (2013.01); *A61M 2205/581* (2013.01); *A61M 2205/583* (2013.01); *A61M 2230/06* (2013.01); *A61M 2230/201* (2013.01); *A61M 2230/202* (2013.01); *A61M 2230/205* (2013.01); *A61M 2230/50* (2013.01); *A61M 2230/65* (2013.01); *G06F 19/345* (2013.01); *G06F 19/3456* (2013.01)

(58) Field of Classification Search
CPC .... A61M 2016/0033; A61M 2230/202; A61M 2205/581; A61M 2230/50; A61M 2230/65; G06F 19/3481; A61B 5/14532; A61B 5/4818; A61B 5/4035
USPC ............ 128/200.24, 203.12, 203.14, 203.15, 128/204.18, 204.21, 204.23, 205.11
See application file for complete search history.

(56) References Cited

U.S. PATENT DOCUMENTS

| | | | | |
|---|---|---|---|---|
| 5,704,345 | A * | 1/1998 | Berthon-Jones | ......... 128/204.23 |
| 7,021,309 | B2 * | 4/2006 | Gonda et al. | ............ 128/200.14 |
| 7,027,871 | B2 | 4/2006 | Burnes et al. | |
| 7,160,252 | B2 | 1/2007 | Cho et al. | |
| 8,640,698 | B2 * | 2/2014 | Darkin | .............. A61M 16/0051 |
| | | | | 128/200.26 |
| 2004/0134496 | A1 * | 7/2004 | Cho et al. | ................. 128/204.23 |
| 2005/0115561 | A1 | 6/2005 | Stahmann et al. | |
| 2005/0192508 | A1 * | 9/2005 | Lange | .................. A61B 5/0823 |
| | | | | 600/534 |
| 2006/0084877 | A1 * | 4/2006 | Ujhazy et al. | ................. 600/483 |
| 2006/0241708 | A1 | 10/2006 | Boute | |
| 2007/0023045 | A1 * | 2/2007 | Kwok et al. | ............. 128/204.23 |
| 2008/0066753 | A1 * | 3/2008 | Martin et al. | ............. 128/204.23 |
| 2008/0188733 | A1 | 8/2008 | Al-Ali et al. | |
| 2008/0306353 | A1 * | 12/2008 | Douglas | .............. G06F 19/3406 |
| | | | | 600/301 |

OTHER PUBLICATIONS

International Search Report, PCT/AU09/00271, dated May 5, 2009.
Leiter, Lawrence, et al. Assessment of the Impact of Fear of Hypoglycemic Episodes on Glycemic and Hypoglycemia Canadian J. Diabetes, 2005; 29(a):186-192.
Meslier, N., et al., Impaired Glucose-Insulin Metabolism in Males with Obstructive Sleep Apnoea Syndrome, Eur Respir J 2003; 22:156-160.
Therapeutic effect of CPAP in patients with sleep apnea syndrome and metabolism syndrome/ Xiao L-i ru, Liu Zhonghua, Shui Ca-i zhen/ / Chinese Journal of Cardiovascular Rehabilitation Medicine, 2008, vol. 17 ( 1 ) : 59-64.
Chinese Office Action for Application No. 200980116055.6 dated Jul. 20, 2012.

* cited by examiner

BLOOD GLUCOSE REGULATION THROUGH CONTROL OF BREATHING

CROSS-REFERENCE TO RELATED APPLICATIONS

The present application claims the benefit of Application Ser. No. 61/068,189, filed Mar. 5, 2008, entitled "D-PAP—A Device for Improved Regulation of Nocturnal Blood Glucose through Control of Breathing During Sleep", the disclosure of which is hereby incorporated herein by reference.

FIELD OF TECHNOLOGY

The present technology involves a device, system or method for improved regulation of blood glucose through control of breathing during sleep; or treatment of diabetes by controlling a patient's breathing.

BACKGROUND OF TECHNOLOGY

Diabetes is a disease characterized by an elevated level of glucose in the blood and in the urine. When blood sugar extremes—both high (hyperglycemia) and low (hypoglycemia)—are not treated, a patient can fall into a diabetic coma. The most common cause of diabetic coma is hypoglycemia. This is caused by excessive treatment with insulin relative to food intake and physical activity. Research indicates that the frequency of severe hypoglycemia is about 1.9 and 2.6 episodes per patient per year for Type 1 and Type 2 diabetes patients, respectively, with approximately 50% of these episodes occurring during sleep. There is evidence that the fear of a hypoglycemic episode significantly affects patient outcomes, such as glycemic control and management, self-treatment modifications, and post-episode lifestyle infringements (see Leiter et al. 2005, *Canadian J. Diabetes;* 29:186-192). Recent studies have indicated that about 30% of diabetic patients also have OSA (Meslier et al, *Eur. Resp. J.,* 22(1):156-160), and there is emerging data indicating that effective treatment of OSA with n-CPAP significantly improves glucose metabolism.

Previously, treatments for diabetes usually have relied upon the either: regulating a patient's diet to limit the levels of glucose or fat ingested and/or monitoring and administering insulin or other pharmaceutical agents to control and regulate the glucose cycles in the body of a patient.

Systems have been described to detect and inform the patient or clinician of an imminent hypoglycemic or hyperglycemic event occurring within the patient due to poor regulation of the glucose pathways. These systems include the descriptions of: U.S. Pat. No. 7,160,252—Cho et al, U.S. Pat. No. 7,027,871—Burnes et al, and Patent Cooperation Treaty (PCT) Published Patent Application No. WO/2007/093010—Darkin et al.

Sleep-Disordered Breathing (SDB) is a general term for a sleep disorder with apneas and hypopneas. Obstructive Sleep Apnea (OSA) is an example of such a sleep disorder. Sullivan invented treatment of OSA with nasal Continuous Positive Airway Pressure (CPAP). See U.S. Pat. No. 4,944,310 (Sullivan). An apparatus for CPAP treatment typically includes: (i) a source of air at positive pressure, such as a servo-controlled blower, flow generator, or other positive airway pressure (PAP) device; (ii) an air delivery conduit; and (iii) a patient interface, such as a mask. The patient interface typically is connected to the patient with headgear including, for example, a series of elastic straps. At least a portion of the headgear is in contact with the patient's skin, typically on the patient's face. Patients wear the apparatus while sleeping.

A basic CPAP device may provide a supply of air at a generally fixed pressure in the range of 4-20 $cmH_2O$. A more advanced CPAP device such as ResMed's AUTOSET SPIRIT™ can monitor the patient's breathing, determine the shape of the breath waveform, detect the presence of snoring, apneas, and hypopneas, and also adjust the treatment pressure. U.S. Pat. No. 5,704,345 to Berthon-Jones et al. describes this in detail. The entire contents of this patent are incorporated herein by reference.

Certain example embodiments of the present technology are directed towards improving patient outcomes with methods and apparatuses that can reduce the patients' fear of hypoglycemia and/or other diabetes-related events.

SUMMARY OF TECHNOLOGY

The present technology may involve a respiratory treatment device, system or apparatus including a flow generator configured to provide respiratory treatment to a patient.

The present technology may also involve an apparatus, device or system described by the above paragraph further including one or more blood glucose condition detectors configured to detect a blood glucose condition of the patient and a controller to adjust a respiratory treatment parameter of the flow generator in response to a blood glucose condition signal of the one or more detectors.

The present technology may involve an apparatus, device or system described by any of the above paragraphs wherein a blood glucose condition detector operates based on any one or combination of (a) one or more respiratory-based measures, (b) one or more sympathetic activation-based measures and (c) one or more peripheral perfusion-based measures.

The present technology may involve an apparatus, device or system described by any of the above paragraphs wherein a blood glucose condition detector comprises one or more of a respiratory-based blood glucose condition indicator, a sympathetic activation-based blood glucose condition indicator and a peripheral perfusion-based blood glucose condition indicator.

The present technology may involve an apparatus, device or system described by any of the above paragraphs further including a direct blood glucose detector to generate a signal representative of a blood glucose level of the patient.

The present technology may involve an apparatus, device or system described by any of the above paragraphs further including a direct blood glucose detector to generate a signal representative of a blood glucose level of the patient and wherein a controller adjusts a respiratory treatment parameter of the flow generator in response to a blood glucose condition signal of the detector.

The present technology may involve an apparatus, device or system described by any of the above paragraphs wherein the device, system or apparatus records blood glucose data from a direct blood glucose detector and data representing one or more respiratory-based measures of the patient, one or more sympathetic activation-based measures of a condition of the patient and one or more peripheral perfusion-based measures of a condition of the patient.

The present technology may involve an apparatus, device or system described by any of the above paragraphs wherein the device, system or apparatus records blood glucose data from a direct blood glucose detector and data representing one or more respiratory-based measures of the patient, one or more sympathetic activation-based measures of a condition of the patient and one or more peripheral perfusion-based measures of a condition of the patient, wherein the measures are recorded utilizing common measurement times.

The present technology may involve an apparatus, device or system described by any of the above paragraphs wherein respiratory treatment parameter of the flow generator is one or more of a breath rate parameter, a breath shape parameter, a tidal volume parameter and end expiratory pressure parameter.

The present technology may involve an apparatus, device or system described by any of the above paragraphs wherein the blood glucose condition detector comprises one or more thresholds determined by an empirical analysis of a relationship between (a) one or more respiratory-based measures and a blood glucose condition, (b) one or more sympathetic activation-based measures and a blood glucose condition and/or (c) one or more peripheral perfusion-based measures and a blood glucose condition.

The present technology may involve an apparatus, device or system described by any of the above paragraphs wherein the one or more respiratory-based measures includes one or more measures of snoring, hypopnea, flow limitation, apnea, respiratory arousal, and/or respiratory measures associated with hypoxemia.

Other aspects, features, and advantages of this technology will become apparent from the following detailed description, claims and figures, which are a part of this disclosure and which illustrate, by way of example, principles of this technology.

BRIEF DESCRIPTION OF DRAWINGS

The accompanying drawings facilitate an understanding of the various embodiments of this present invention. In such drawings.

DETAILED DESCRIPTION OF EMBODIMENTS

Figure 1:
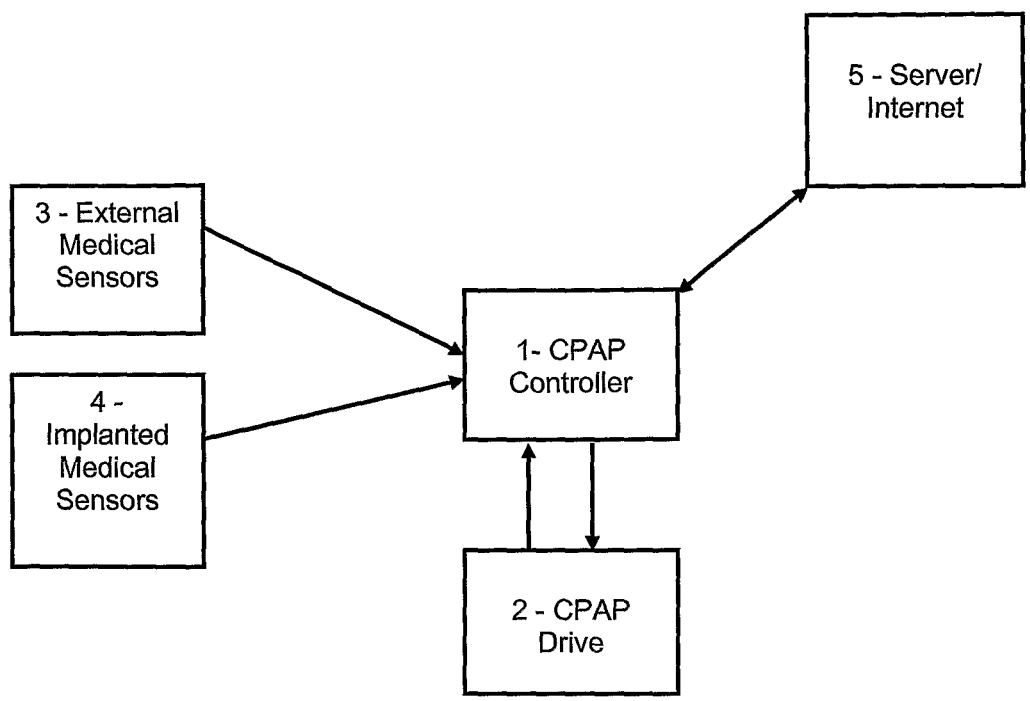
FIG. 1 depicts a schematic representation of system or device described as an embodiment of the present invention.

Sleep disordered breathing is a systemic condition with cardiovascular, endocrine and metabolic interactions. Specifically, sleep apnea is associated with glucose intolerance and insulin resistance and may be causally related to the development of Type 2 Diabetes Mellitus, but may also impact Type I Diabetes Mellitus.

Sleep apnea is associated with recurrent sleep fragmentation and intermittent hypoxemia, which may mediate the metabolic disturbance. It has been suggested that sleep fragmentation and hypoxia caused by sleep apnea create a cascade of events:

1. Activation of adipose cells to secrete leptin, tumor necrosing factor-α (TNF-α) and interleukin-6 (IL-6). The inflammatory cytokines produced by the adipose tissue, may cause glucose intolerance and damage to the vasculature associated with hypertension, cardiovascular and cerebrovascular disease.
2. Sympathetic Nervous System activation; which can impact directly on hepatic glucose production and indirectly on lipolysis and the release of free fatty acids that can contribute to insulin resistance.
3. Hypothalamo-pituitary-adrenal activation, impacting on the release of growth hormone, catacholamines and cortisol, which in turn are counter-regulatory hormones in glucose metabolism, impacting on glucose intolerance and insulin resistance.

The tight regulation of blood glucose levels is the primary aim of diabetes management and care, as poor regulation of blood glucose levels is the primary contributor to diabetic complications such as peripheral neuropathy, diabetic retinopathy and heart disease. Daytime blood glucose levels are carefully managed by directly monitoring blood glucose levels (finger prick test), meal planning, oral medications and for some patients insulin injection (insulin dependent Type 2 diabetes). Type 1 diabetes mellitus is routinely managed through insulin injection.

Nocturnal blood glucose levels are not easily managed with current approaches, however, leading to hyperglycemia (Type 2) or risk of hypoglycemia (in Type 1 and insulin dependent Type 2 diabetes), thereby contributing to disease progression and the development of diabetic complications.

Conventional Continuous Positive Airway Pressure ('CPAP') therapy can improve insulin resistance in Type 2 diabetes mellitus. The technology described here may be a further improvement on standard CPAP therapy, which may lead more directly to improved nocturnal blood glucose regulation and improved insulin resistance.

An example embodiment of the present technology may include: a device, method or system for the improvement of nocturnal blood glucose regulation through the control of breathing during sleep. Typically, the embodiment may implement an algorithm of the methods and systems herein discussed with reference to a controller for respiratory treatment device. A respiratory treatment device may include: a CPAP machine, an APAP machine, bi-level flow generator, ventilator or other patient treatment device configured to provide a controlled flow of breathable gas from a flow generator to a patient's respiratory system.

In an example embodiment of the present technology, a closed loop therapy has two primary components:
1. at least one measurement component and
2. a drive component.
1. Measurement Component:
(a) Respiratory Based Detection In some embodiments, measurement involves extracting features from respiratory flow and/or pressure signals that are correlated with, or predictive of, changes in blood glucose level. Respiratory flow and pressure are measurable by CPAP or comparable machines configured with pressure and/or flow sensors.

Respiratory features may include, but are not limited to, measures of snoring, hypopnea, flow limitation, apnea, other measures of respiratory arousal (e.g., respiratory features associated with hypoxemia).

The features are selected for their correlation or predictive association with blood glucose levels and blood glucose dynamics. The associations may be identified empirically using traditional statistical analysis, pattern recognition or artificial intelligence methods (including artificial neural networks). These respiratory-based features, which may be indicative of blood glucose levels and/or blood glucose dynamics, can be implemented as part of a respiratory-based blood glucose condition detector, such as a detector implemented with software of a processor-based system or similar circuit based design.

For example, the one or more of the respiratory-based features may be utilized as a respiratory-based blood glucose condition indicator. The respiratory-based features, which may be one or more indices of the measured respiratory-based features, may be compared with one or more thresholds that have been calibrated or tested for an association with a condition or change in blood glucose levels of a patient utilizing the respiratory treatment device. The relationship of the indices to the thresholds may then be utilized as the indicator for signaling changes of a blood glucose condition of the patient. The indicator and/or the changes thereto maybe monitored and/or recorded to inform the patient and/or physician of the change. Moreover, the indicator and/or the changes thereto may be utilized to trigger or control a change to treatment based on a control algorithm such as that discussed in more detail herein.

(b) Sympathetic Activation Based Detection

Sympathetic activation of the nervous system is associated with sleep fragmentation and hypoxia and contributes to increased glucose production and insulin resistance. Sympathetic activation may be measured non-invasively. For example, a non-invasive hypoglycemia monitor may be utilized, such as the device manufactured by AiMedics. Moreover, a hyperglycemia and/or hypoglycemia monitor such as the monitor described in International Patent Application Publication No. WO/2007/093010 may also be utilized. Another suitable device may be a SenseWear™ device manufactured by BodyMedia, Inc. or similar, which measures or monitors sympathetic activation.

Preferably, in addition to respiratory parameters, or alternatively, the measurement method may consist of deriving features from measures of sympathetic activation e.g., galvanic skin response, skin temperature and heart rate, that are associated with changes in blood glucose level.

Preferably, the sympathetic activation features are selected for their correlation or predictive association with blood glucose levels and blood glucose dynamics. The associations may be identified empirically using traditional statistical analysis, pattern recognition or artificial intelligence methods. These sympathetic activation-based measures, which may also be indicative of blood glucose levels and/or blood glucose dynamics, can be implemented as part of a sympathetic activation-based blood glucose condition detector, such as a detector implemented with software of a processor-based system.

For example, the one or more of the sympathetic activation-based features may be utilized as a sympathetic activation-based blood glucose condition indicator like the respiratory-based blood glucose condition indicators previously discussed and may be based on thresholds determined empirically. Moreover, these indicators may be combined with the respiratory-based indicators to provide yet further blood glucose condition indicators. These may also be monitored and/or recorded and utilized to trigger or control changes to treatment.

(c) Peripheral Perfusion Based Detection:

Diabetes is associated with impaired peripheral perfusion e.g., diabetic foot. The impact on perfusion may be detected by analyzing changes in the morphology of measures of peripheral perfusion of $0_2$ (measured using oxymetry) and transcutaneous $CO_2$. Therefore, in addition to respiratory parameters and measures of sympathetic activation, or alternatively, the measurement method may consist of deriving features from measures of peripheral perfusion e.g., oxymetry and $TCO_2$, that are correlated with or predictive of changes in blood glucose level.

Preferably, the perfusion features are selected for their correlation or predictive association with blood glucose levels and blood glucose dynamics. The associations may be identified empirically using traditional statistical analysis, pattern recognition or artificial intelligence methods.

The respiratory, sympathetic activation and perfusion features may be used singularly or in combination.

These peripheral perfusion-based measures, which may be indicative of blood glucose levels and/or blood glucose dynamics, can be implemented as part of a peripheral perfusion-based blood glucose condition detector, such as a detector implemented with software of a processor-based system or similar circuit based design.

For example, the one or more of the peripheral perfusion-based features may be utilized as a peripheral perfusion-based blood glucose condition indicator like the respiratory-based blood glucose condition indicators previously discussed and may be based on thresholds determined empirically. Moreover, these indicators may be combined with the respiratory-based blood glucose condition indicators and/or sympathetic activation-based blood glucose condition indicators to provide yet further blood glucose condition indicators. These may also be monitored and/or recorded and utilized to trigger or control changes to treatment.

(d) Direct Blood Glucose Detection

Alternatively, or in conjunction with any of the prior detectors, the measurement component may consist of a blood glucose monitor that may more directly measure blood glucose levels such as a device that monitors blood glucose levels via a subcutaneous or other semi-invasive sensor. Such a detector can provide output data signals representative of blood glucose levels or conditions that may be supplied to a control system or a respiratory treatment device as discussed in more detail herein. Moreover, such output signals may be input to a common monitor or data analysis system that also receives data from one or more of the previously discussed detectors for comparing relative data from the various detectors and/or for calibrating one or more of the signals or detection output of the particular detectors to a particular patient and/or determining thresholds associated with the data from the previously described detectors. Thus, the analysis system may record or permit recording of data from the monitor and the detectors on a common time scale or a common times so that the data may be compared.

2. Drive Component:

A number of hormones affect respiratory dynamics directly. The carotid body has a direct role in respiratory control and has a probable role in glucose metabolism.

The drive method modulates breathing by controlling a respiratory treatment device which may be based on output data from one or more, or any combination of the above described detectors and indicators, to indirectly manipulate blood glucose levels through the relationship between hormones and breathing.

Respiratory drive parameters of the respiratory treatment device that may be altered include, but are not limited to, breath rate, breath shape, tidal volume and end expiratory pressure.

The relationship between particular drive parameter adjustments and the impact on blood glucose levels may be determined empirically.

For example, based on the detected condition change from any combination of one or more of the indicators described above, a respiratory treatment device may increase a respiratory drive parameter, such as increasing a delivered tidal volume or increasing an end expiratory pressure. The treatment changes implemented by the respiratory treatment device may be performed in a closed loop control fashion to maintain the indicators at or within desired levels. Optionally, such treatment changes may be implemented in an open loop fashion such as by implementing a limited-time predetermined treatment response based on output of the detector(s) such as making a predetermined set of changes to the treatment control parameters for a remainder of a treatment session (e.g., a night's sleep session):

Optionally, the respiratory treatment device may also be controlled by a traditional treatment control regimen associated with treating respiratory conditions, such as sleep disordered breathing.

In an further embodiment, closed loop control with the respiratory treatment device may implement regulation of nocturnal blood glucose levels in Type 2 diabetes, may be improved by altering the respiratory drive delivered by a CPAP machine, in response to the detection of any combination of respiratory and/or sympathetic activation features and/or peripheral perfusion features associated with (correlated with, predictive of, or otherwise indicative of) poor blood glucose regulation.

The method may not be limited to use in the presence of mild to severe OSA, but may also be beneficial in the regulation of nocturnal blood glucose levels associated with sub-clinical indications of sleep disordered breathing, snoring or the absence of sleep disorder breathing altogether.

The method may easily be adapted or extended to the benefit of Type 1 diabetes mellitus and other endocrine and metabolic disorders, such as leptin resistance.

Although the technology herein has been described with reference to particular embodiments, it is to be understood that these embodiments are merely illustrative of the principles and applications of the technology. It is therefore to be understood that numerous modifications may be made to the illustrative embodiments and that other arrangements may be devised without departing from the spirit and scope of the technology.

By way of further example, the present embodiments may also involve an apparatus, device, method or system described by any of the above paragraphs wherein the apparatus, device or system is further configured as a CPAP machine, APAP machine, bi-level flow generator and/or ventilator.

The present embodiments may also involve an apparatus, device or system described by any of the above paragraphs wherein the apparatus, device or system implements a closed loop controlled regulation of nocturnal blood glucose levels by controlling changes in respiratory therapy delivered by the flow generator.

The present embodiments may also involve a method of treating a patient and/or measuring a condition of a patient as described by any of the above paragraphs.

Further Embodiments

Figure 2:
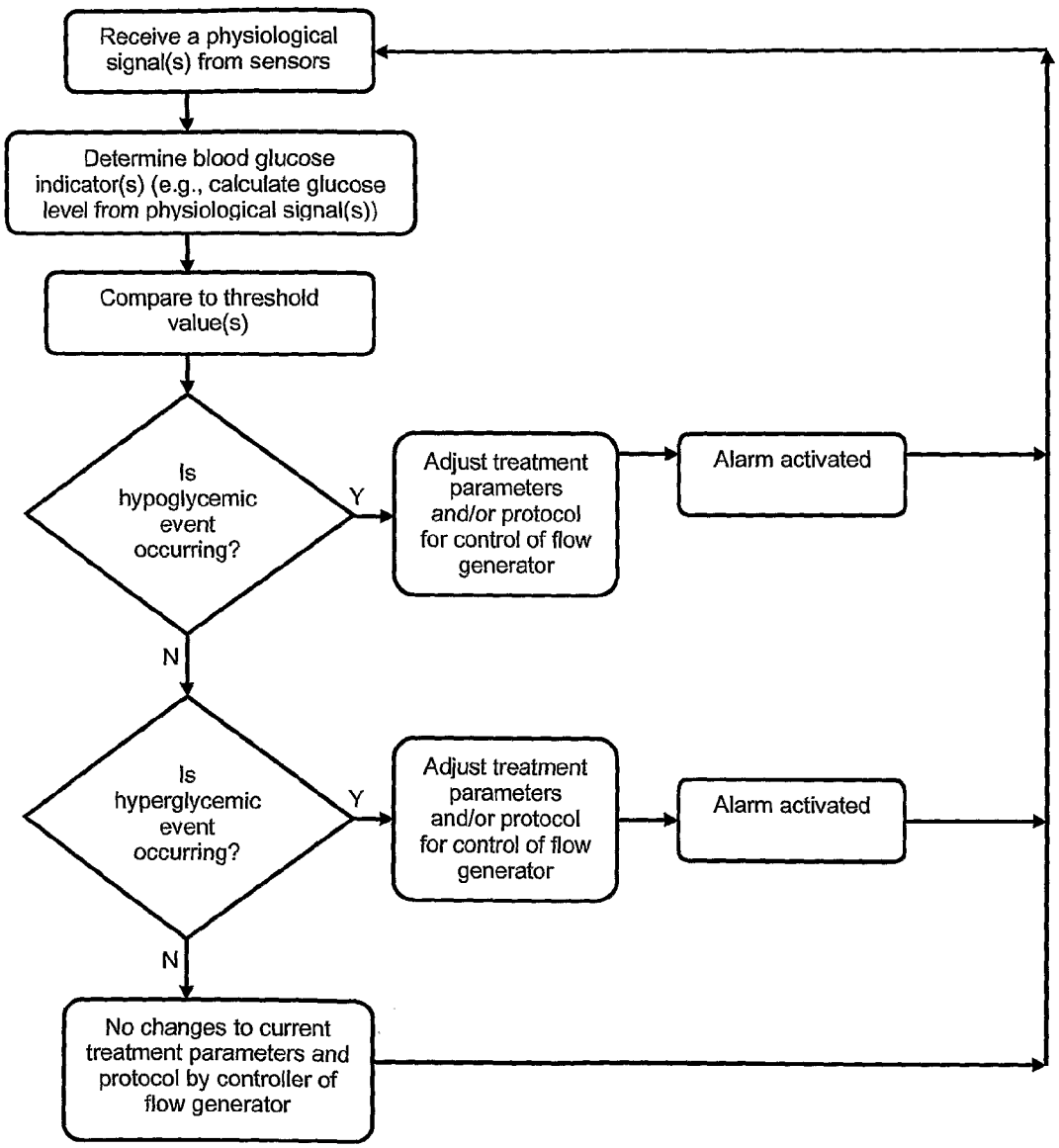
FIG. 2 depicts a flow chart representation of an example methodology to be used as part of an embodiment of the present invention.

A further embodiment of the present technology is depicted in FIGS. 1 and 2. FIG. 1 shows a schematic view of example components of a system or device of the present technology. The system or device may optionally implement the method of FIG. 2.

In FIG. 1, a positive airway pressure device or a CPAP device is included comprising: a CPAP controller 1 (e.g., a control circuit and/or microprocessor with memory storage and software therein to implement the control methodologies or algorithms discussed herein) and a CPAP drive unit 2. Preferably, the CPAP is connected to a patient and may provide PAP as a treatment for both OSA and blood glucose regulation for the treatment of Diabetes. Preferably, the treatment is provided to the patient during their normal sleep periods. Whilst the present embodiment is directed to the control and use of CPAP, other forms of mechanical ventilation may be able to use same or similar control methodology, system or device. The controller may optionally serve as, or be part of, a blood glucose condition detector as discussed herein.

The CPAP Drive 2 comprises of a mask assembly (not shown) in air communication with a blower or air flow generator (not shown). The blower is operated by the CPAP controller 1 which sends control signals to the CPAP drive unit 2 for meeting pressure, speed, and/or flow set-points etc. to provide optimal support for specific circumstances.

Preferably, the CPAP drive unit 2 also may include flow and/or pressure sensors in the air-path to detect air flow or pressure either in the blower or in the mask assembly, depending on the location and positioning of the sensors. This flow and/or pressure data is electronically sent to the CPAP controller 1.

The CPAP Controller 1 may use the flow and/or pressure sensors as an analogue of particular pieces of physiological data in relation to the patient's current state of health such as those previously discussed with regard to the blood glucose condition indicators.

Additionally, the CPAP controller may also be electrically connected to at least one external medical sensor 3. These external medical sensors 3 may non-invasively detect physiological data about the patient and may include specific data relating to skin detected electro-potentials, non-invasive oximetry or glucose level detection, heart rate, respiration and numerous other forms of externally available data. The data detected by the external medical sensors is transmitted or sent to the CPAP controller. Thus, the external medical sensor(s) may optionally serve as, or be part of, a blood glucose condition detector as previously discussed.

Implanted or internal medical sensors 4 may also be used in conjunction with the current embodiment. Preferably, the implanted medical sensors may transmit physiological data and information to the CPAP controller 1. This information may be used in a similar way to the formation provided by the external medical sensors 3. One of the advantages of using implanted medical sensors 4 is that direct glucose level monitoring may be achieved and the results of this physiological data may transmitted directly to the CPAP controller 1. Thus, the internal medical sensor(s) may optionally serve as, or be part of, a blood glucose condition detector as previously discussed.

Preferably, the CPAP controller may be selectively connected to a computer (such as a server computer) or a communications network such as an internet 5. This connection may allow for physiological data to be transmitted or recorded on a computer system other than the controller 1. Preferably, this data could be directly sent via the internet to clinician or medical staff in case of an emergency or routine maintenance or patient check ups. Preferably, the remote connection by the server or internet 5 may allow for the setting of the CPAP controller 1 to be updated or the control parameters or threshold value amended or changed, by a clinician at a distal location relative to the patient. Also the clinician could be notified of problems remotely by the server sending SMS messages or emails to clinician. Thus, the external computing system(s) may optionally serve as, or be part of, a blood glucose condition detector as previously discussed.

Preferably, all of the electrical connections between the various modules shown or depicted in FIG. 1 may be achieved wirelessly. Standard wireless protocols may be suitable for this type of transmission, furthermore several wireless protocols may be also additional encrypted to provide a security and error free transmission. Wireless transmission of data is the preferred transmission means for the implanted medical sensors 4 or the server/internet connection 5.

Figure 3:
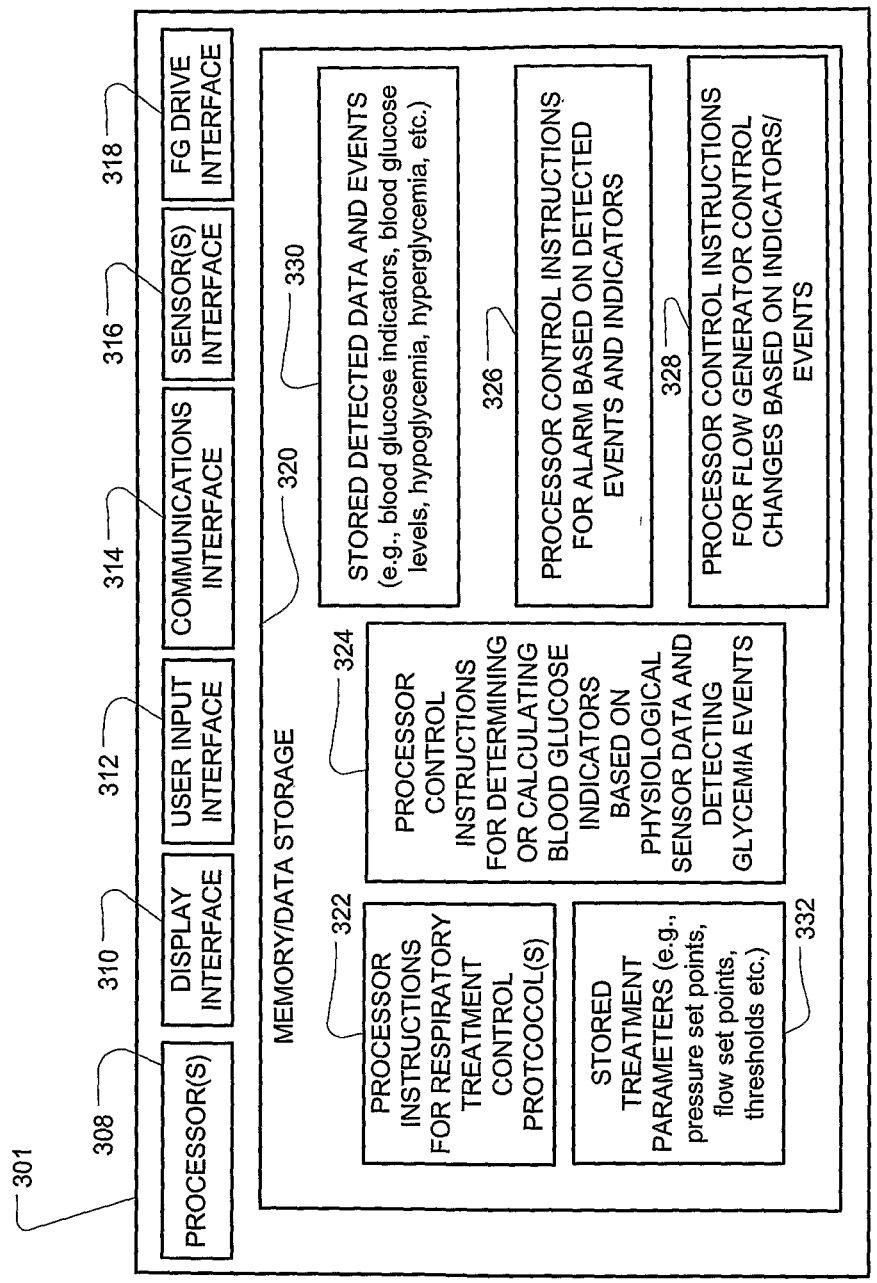
FIG. 3 illustrates a controller for an embodiment of a respiratory treatment device of the present technology.

By way of example, a controller 301 for an embodiment of the respiratory treatment device is illustrated in FIG. 3. The controller 301 of FIG. 3 typically includes one or more processors 308 such as a digital processor and/or application specific integrated circuits (ASIC). The controller 301 may also include circuits comprising an output display interface 310, user input interface 312, communications interface 314, sensors interface 316 and a flow generator drive interface 318. In this example, the controller 301 further includes memory 320 or data storage circuits for the operations of the controller. Thus, the processors will typically be configured to implement the particular control methodologies such as the algorithms described in more detail herein. For example, the memory may include processor control instructions of one or more respiratory treatment protocols 322. It may also include processor control instructions for determining or calculating blood glucose condition indicators based on physiological sensor data and detecting glycemia events 324. It may further include processor control instructions for alarm generation based on detected events and indicators 326 as previously discussed. Similarly, it may include processor control instructions for flow generator control changes based on detected indicators and events 328 as discussed herein. For these ends, the memory may also include historic detected indicators and events 330 determined by the processors. The memory may also include stored treatment parameters 332.

FIG. 2 depicts in a flow chart steps that may be taken by the CPAP controller 1 in regard to its methodology for this embodiment of the technology.

The step as illustrated in FIG. 2, is for the controller to receive, the physiological signals or data from the remote sensors. The controller then processes this data and may determine a blood glucose condition indicator such as by calculating the blood glucose level of the patient from the physiological data.

The controller then compares the measured or calculated blood glucose level with standard predefined threshold values. Typically, the minimum or lower threshold value may be approximately between about 2 to 3.5 mmol/L. The upper or maximum threshold value may be about 5.6 to 9 mmol/L. Alternatively, or in addition thereto, a presently calculated blood glucose level may be compared to one or more previously calculated levels or an average thereof where the previously calculated levels are determined by the device for the patient earlier in treatment session or from a prior session. Similarly, other blood glucose condition indicators may be processed and compared with standard and/or previously determined/calculated thresholds.

If the measured or calculated value of blood glucose is above the maximum threshold value, the controller may determine that a hyperglycemic event is currently occurring, at the measured time. Alternatively, or in addition thereto, if the presently calculated blood glucose level has changed with respect to the previously determined level by more than a predetermined amount, such as a significant increase, a hyperglycemic event may be detected as occurring. A similar assessment may optionally be implemented with the other blood glucose condition indicators and related standard and/or previously calculated thresholds.

If the measured or calculated value of blood glucose is below the minimum threshold value, the controller may determine that a hypoglycemic event is currently occurring, at the measured time. Alternatively, or in addition thereto, if the presently calculated blood glucose level has changed with respect to the previously determined level by more than a predetermined amount, such as a significant decrease, a hyperglycemic event may be detected as occurring. A similar assessment may optionally be implemented with further assessment of the other blood glucose condition indicators and related standard and/or previously calculated thresholds.

According to the methodology depicted in FIG. 2 the controller then may implement a change to the pressure treatment control protocol of the flow generator by changing the control signals sent to the CPAP drive unit. For example, such a change of treatment protocol may cause the flow generator to discontinue a continuous positive airway pressure treatment protocol (e.g., a protocol where the pressure is controlled to generally remain constant over a breathing cycle of a patient) and to start controlling varying the pressure over the patient's respiratory cycle in a manner that more closely replicates a breathing cycle to provide support to the patient (e.g., bi-level pressure changes or a smooth pressure waveform). Further, the controlled treatment protocol change may result in the device beginning to control the flow generator to satisfy a target ventilation, such as a minute ventilation, by comparing a measure of ventilation determined with the controller and a target ventilation. Still optionally, the controller may change a flow or pressure treatment parameter of a current treatment protocol based on any of the detected events such as by increasing or decreasing a pressure setting, a flow setting, a ventilation target, etc. by a suitable amount.

Optionally, the controller may adjust the treatment parameters provided by the flow generator to treat Kussmaul breathing based on detecting a Kussmaul breathing event. For example, if a measure of patient ventilation and/or respiratory rate changes with respect to a set of thresholds associated with Kussmaul breathing (i.e., indicative of a patient experiencing initially rapid and shallow breathing followed by deep, slow and labored breathing) a change in the treatment parameters may be triggered.

In a case of either a hypoglycemic or hyperglycemic event detection based on any one or more of the blood glucose condition indicators, the controller may optionally issue an alarm. The alarm may be an audible and/or visual alarm (e.g., a speaker and/or light, LED or display) connected to the controller. Also, the alarm may involve sending a message via a means of electronic communication to the aforementioned remote clinician through a communications device of the controller.

If neither hypoglycemia nor hyperglycemia are detected, the controller may continue to provide PAP in accordance with standard treatments for OSA. Preferably, the methodology of the flow chart of FIG. 2 may be repeated in a loop fashion. Optionally, if such events are not detected for a period of time, the treatment protocol may be changed to return to the treatment protocol that was applied prior to the detection of the hypoglycemia or hyperglycemia events.

Optionally, the loop control methodology shown in FIG. 2 may be performed at predetermined time intervals which may be varied to suit the particular circumstances of the patient being treated. Still optionally, the methodology may continuously cycle.

In some embodiments, the controller may control the CPAP drive unit to cause the flow generator to normalize the respiration of the patient. The controller may accomplish this by incrementally adjusting the flow rate generated by the flow generator or CPAP drive unit in accordance with the current detected or calculated blood glucose level of the patient. For example, a change in blood glucose level or blood glucose condition indicator by a predetermined amount may serve as a function for a step change to a target ventilation parameter. With each such detected change to the glucose indicator, a further step adjustment to the ventilation target may be implemented. Similarly, changes may be implemented to triggering and cycling parameters (e.g. start of either inspiration or expiration pressure level delivery), etc. based on the changes in the blood glucose indicators.

By way of further example, in the event of a change to a blood glucose condition indicator, such as a sympathetic activation-based blood glucose condition indicator, respiratory treatment parameters may be adjusted as a more continuous function of the change. For example, in the case of controlling an adjustment to a target ventilation parameter, the target ventilation parameter may be set as a proportional function (e.g., directly or inversely) of the blood glucose condition indicator. In one such embodiment, the target ventilation may be calculated as a multiple of the blood glucose condition indicator (e.g., target_ventilation= (BGI*1/X) or (BGI*X) where BGI is a calculated blood glucose condition indicator and X is an adjustment factor that depends on the ventilation measure being controlled.)

Furthermore, the controller may be adapted to treat Kussmaul breathing prior to its occurrence. For example, a measure of patient ventilation and/or respiratory rate changes with respect to a set of thresholds associated with the onset of Kussmaul breathing (i.e., indicative of a patient experiencing initially rapid and shallow breathing) may be analyzed. This set of conditions taken alone, or in conjunction with a detected change in a calculated blood glucose level or a blood glucose condition indicator, may be considered an onset of Kussmaul breathing. Such a detected event may implement or trigger a change in the respiratory treatment parameters (e.g. an increase a target ventilation) or a change in protocol (e.g., from a continuous positive airway pressure protocol to a target ventilation protocol) that is controlled and delivered by the device.

Optionally, in some embodiments, the implanted medical sensors may include one or more dermal sensors implanted or encapsulated within the patient interface so that they may touch the patient's skin layer during use of the patient interface. Based on the contact, they may then detect physiological data that may be used to calculate the patient's blood glucose level or further blood glucose condition indicators. An example of a suitable dermal sensor may be a dermal patch sensor or transdermal monitor such as the Abbott FreeStyle Navigator. The Abbott FreeStyle Navigator is a continuous glucose monitoring system.

Furthermore, in some embodiments, a chemical sensor may be integrally or selectably attachable to the patient interface. This chemical sensor may detect chemicals produced in the patient's breath that may be indicative of hypoglycemia or hyperglycemia. These sensors may include ones that are capable of detecting ketone bodies or other chemicals generated and given off in the breath of patient's experience abnormal glucose levels.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments, e.g., aspects of one embodiment may be combined with aspects of another embodiment to realize yet other embodiments.

Also, the various embodiments described above may be implemented in conjunction with other embodiments, e.g., aspects of one embodiment may be combined with aspects of another embodiment to realize yet other embodiments. In addition, while the invention has particular application to patients suffering from OSA and diabetes, it is to be appreciated that patients suffering from other illnesses (e.g. congestive heart failure, morbid obesity, stoke, bariatric surgery, etc) can derive benefit from the above teachings. Moreover, the above teachings have applicability with patients and non-patients alike in non-medical applications.

The invention claimed is:

1. A device for treating sleep disordered breathing and diabetes comprising:
at least one sensor detecting a physiological signal and transmitting physiological data to a controller; and
a controller to control an air flow generator to provide pressurized air to a patient according to a first treatment protocol, and wherein said controller is adapted to determine a blood glucose level from the physiological data and to change to controlling the air flow generator to provide pressurized air according to a second treatment protocol based on the determined blood glucose level, wherein the first treatment protocol controls pressure to generally remain constant over a breathing cycle of the patient, and wherein the second treatment protocol controls the pressure to vary over the breathing cycle of the patient and comprises initiating target ventilation control.

2. The device of claim 1, wherein the controller compares the determined blood glucose level to one or more thresholds.

3. The device of claim 2 wherein the one or more thresholds comprises a minimum threshold value and a maximum threshold value.

4. The device of claim 3, wherein the minimum threshold value is within a range of about 2 to 3.5 mmol/L.

5. The device of claim 3, wherein the maximum threshold value is within a range of about 5.6 to 9 mmol/L.

6. The device of claim 3, wherein said controller activates an alarm, when blood glucose level is below the minimum or above the maximum threshold values.

7. A device for treating sleep disordered breathing: wherein said device includes a patient interface, an air flow generator configured to provide pressurized gas and operated by a controller and at least one sensor connected to the controller, wherein said controller determines glucose levels from a detected breathing pattern of a patient and then adjusts a target ventilation parameter of the air flow generator based on the determined glucose levels.

8. A method in a controller of a respiratory treatment device for treating sleep disordered breathing and diabetes, the method comprising:
sensing a physiological signal of a patient;
determining blood glucose level from the physiological signal; and changing a first treatment protocol for controlling a flow generator to provide pressurized air to a second treatment protocol for controlling the flow generator to provide pressurized air based on the blood glucose level, wherein the first treatment protocol controls pressure to generally remain constant over a breathing cycle of the patient, and wherein the second treatment protocol controls the pressure to vary over the breathing cycle of the patient and comprises initiating target ventilation control.

9. The method of claim 8, wherein said method further includes analyzing the determined blood glucose level with respect to a minimum and maximum threshold value.

10. A respiratory treatment apparatus comprising:
a flow generator to provide a flow of breathable air at a pressure above atmospheric to a patient interface according to a first treatment protocol, wherein the first treatment protocol controls pressure to generally remain constant over a breathing cycle of the patient;
a detector to determine a blood glucose condition indicator with at least one sensor;
a controller to change to controlling the flow generator to provide the flow of breathable air at a pressure above atmospheric to the patient interface according to a second treatment protocol based on the detected blood glucose indicator, wherein the second treatment protocol controls the pressure to vary over the breathing cycle of the patient and comprises initiating target ventilation control.

11. The respiratory treatment apparatus of claim 10 wherein the blood glucose condition indicator is a respiratory-based blood glucose condition indicator.

12. The respiratory treatment apparatus of claim 10 wherein the blood glucose condition indicator is a sympathetic activation-based blood glucose condition indicator.

13. The respiratory treatment apparatus of claim 10 wherein the blood glucose condition indicator is a direct blood glucose level.

14. The respiratory treatment apparatus of claim 10 further comprising a Kussmaul breathing pattern detector.

15. The respiratory treatment apparatus of claim 10 wherein an adjustment by the controller based on the detected blood glucose indicator comprises an increase of a ventilation control parameter.

16. The respiratory treatment apparatus of claim 10 wherein an adjustment by the controller based on the detected blood glucose indicator comprises a decrease of a ventilation control parameter.

17. A respiratory treatment apparatus comprising:
flow generation means for providing air flow at a pressure above atmospheric to a patient interface according to a first treatment protocol, wherein the first treatment protocol controls pressure to generally remain constant over a breathing cycle of the patient;
detection means for determining a blood glucose condition indicator;
processing means for changing the flow generation means to provide air flow at a pressure above atmospheric to the patient interface according to a second treatment protocol based on the determined blood glucose condition indicator, wherein the second treatment protocol controls the pressure to vary over the breathing cycle of the patient and comprises initiating target ventilation control.

18. The respiratory treatment apparatus of claim 17 wherein the blood glucose condition indicator is a respiratory-based blood glucose condition indicator.

19. The respiratory treatment apparatus of claim 17 wherein the blood glucose condition indicator is a sympathetic activation-based blood glucose condition indicator.

20. The respiratory treatment apparatus of claim 17 wherein the blood glucose condition indicator is a direct blood glucose level.

21. The respiratory treatment apparatus of claim 17 further comprising a Kussmaul breathing pattern detector.

22. A positive pressure respiratory airway treatment device comprising:
a flow generator including a blower and servo, the flow generator configured to provide a flow of air at a pressure above atmospheric to a patient interface according to a first treatment protocol, wherein the first treatment protocol controls pressure to generally remain constant over a breathing cycle of the patient;
sensor apparatus comprising at least one of a noninvasive hyperglycemia/hypoglycemia monitor, an oximeter, a subcutaneous or semi-invasive blood glucose monitor, the sensor apparatus to generate signals at least representative of one or more physiological characteristics;
a processor to receive signals from the sensor apparatus and control the flow generator, the processor being programmed with processor control instructions, the processor control instructions comprising:
controlling determining of a blood glucose condition indicator; and
controlling a change of the flow generator to provide a flow of air at a pressure above atmospheric to the patient interface according to a second treatment protocol based on the determined blood glucose condition indicator, wherein the second treatment protocol controls the pressure to vary over the breathing cycle of the patient and comprises initiating target ventilation control.

23. The device of claim 22 wherein the blood glucose condition indicator is a respiratory-based blood glucose condition indicator.

24. The device of claim 22 wherein the blood glucose condition indicator is a sympathetic activation-based blood glucose condition indicator.

25. The device of claim 22 wherein the blood glucose condition indicator is a direct blood glucose level.

* * * * *